United States Patent [19]

Kalden et al.

[11] Patent Number: 5,334,612

[45] Date of Patent: Aug. 2, 1994

[54] PHARMACEUTICAL COMPOSITIONS CONTAINING AS ACTIVE SUBSTANCE SULPHUR-CONTAINING CARBOXYLIC ACIDS AND THEIR USE IN COMBATING RETROVIRUSES

[75] Inventors: Joachim Kalden, Erlangen; Bernhard Fleckenstein, Wiesenthau; Andreas Baur; Thomas Harrer, both of Erlangen, all of Fed. Rep. of Germany

[73] Assignee: ASTA Pharma Aktiengesellschaft, Frankfurt, Fed. Rep. of Germany

[21] Appl. No.: 610,560

[22] Filed: Nov. 8, 1990

[30] Foreign Application Priority Data

Nov. 9, 1988 [DE] Fed. Rep. of Germany ....... 3937325
May 16, 1990 [DE] Fed. Rep. of Germany ....... 4015728

[51] Int. Cl.⁵ ................. A61K 31/385; A61K 45/02; A61K 31/385; A61K 37/66
[52] U.S. Cl. ................. 514/440; 514/557; 514/558; 514/559; 514/707; 424/439
[58] Field of Search ............... 514/430, 439, 440, 557, 514/558, 559, 707, 762; 424/439

[56] References Cited

U.S. PATENT DOCUMENTS 2,840,505  6/1958  Grunert et al. ............... 514/440
2,933,430  4/1960  Rosenberg .................... 514/440
5,084,481  1/1992  Ulrich et al. ................. 514/440

FOREIGN PATENT DOCUMENTS 901960    6/1972  Canada .
60-184011 9/1985  Japan ........................... 514/440

OTHER PUBLICATIONS

Conn et al. "Outlines of Biochemistry" John Wiley & Sons, New York, 1987, pp. 181–182.

*Primary Examiner*—Nathan M. Nutter
*Attorney, Agent, or Firm*—Cushman, Darby & Cushman

[57] ABSTRACT

Pharmaceutical compositions containing at least one compound of Formula I,

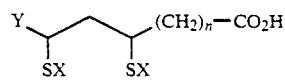

where X is a hydrogen atom or both X's represent a direct link between the two sulphur atoms; Y is hydrogen or $C_1$–$C_6$ alkyl and n represents a number from 1 to 10, or their pharmaceutically acceptable salts including α-lipoic acid and dihydrolipoic acid. The pharmaceutical compositions are useful for the treatment of diseases caused by retroviruses.

22 Claims, 3 Drawing Sheets

Fig. 1 INFLUENCE OF α-LIPOIC ACID (70 μg/ml) ON PERMANENTLY INFECTED MOLT-4 CELLS. THE REDUCTION IN REVERSE TRANSCRIPTASE COUNTS AND IN COUNTED PLAQUES IS GIVEN IN % OF THE POSITIVE CONTROL.

Fig. 2 INFLUENCE OF α-LIPOIC ACID (35 µg/ml) IN COMBINATION WITH RECOMBINANT α-INTERFERON (70 ENZYME UNITS/ml) ON FRESHLY INFECTED JURKAT CELLS. THE REDUCTION IN REVERSE TRANSCRIPTASE COUNTS IS SHOWN IN % OF THE POSITIVE CONTROL.

Fig. 3 INFLUENCE OF α-LIPOIC ACID (35 μg/ml) IN COMBINATION WITH RECOMBINANT α-INTERFERON (70 ENZYME UNITS/ml) ON FRESHLY INFECTED JURKAT CELLS. THE REDUCTION IN COUNTED PLAQUES IS SHOWN IN % OF THE POSITIVE CONTROL.

PHARMACEUTICAL COMPOSITIONS CONTAINING AS ACTIVE SUBSTANCE SULPHUR-CONTAINING CARBOXYLIC ACIDS AND THEIR USE IN COMBATING RETROVIRUSES

The present invention relates to pharmaceutical compositions and processes for their preparation. These pharmaceutical compositions contain active ingredients which are for example suitable for combating retroviruses (for example HIV viruses) and also disorders caused by retroviruses.

In particular the invention relates to the following pharmaceutical compositions and processes for their preparation:

A. Pharmaceutical compositions containing at least one compound of Formula I, where X is a hydrogen atom or both X's represent a direct link between the two sulphur atoms; Y is hydrogen or $C_1$-$C_6$-alkyl and n represents a number from 1 to 10, or their pharmaceutically acceptable salts with the exception of α-lipoic acid and dihydrolipoic acid. The dosage unit for solid or semi-solid formulations of these compounds contain 20 mg to 6 g, in particular 50 mg to 2 g, preferably 100 mg to 1 g or also 400 mg or 500 mg to 1 g of the total amount of active substance I (when used against AIDS preferably also 400 mg to 4 g, in particular 1 g to 3 g of the total amount of active substance I), or solutions, suspensions or emulsions which contain 0.2 mg to 800 mg per ml, preferably 10 mg to 500 mg, in particular 40 mg to 200 mg per ml of the total amount of active substance I or a pharmaceutically acceptable salt thereof.

B. Pharmaceutical compositions containing α-lipoic acid in a dosage unit for solid or semi-solid formulations which contains 51 mg to 6 g, in particular 100 mg to 2 g, preferably 200 mg to 1 g or also 400 mg or 500 mg to 1 g of α-lipoic acid or a pharmaceutically acceptable salt thereof, or in the form of injection solutions which contain 26 mg to 500 mg per ml, preferably 50 mg to 200 mg, in particular 100 mg per ml of - lipoic acid or a pharmaceutically acceptable salt thereof or drinkable solutions, suspensions or emulsions which contain 0.2 mg to 500 mg per ml, preferably 1 mg to 50 mg per ml, in particular 5 mg to 10 mg per ml of α-lipoic acid or a pharmaceutically acceptable salt thereof.

C. Pharmaceutical compositions containing dihydrolipoic acid in a dosage unit for solid or semi-solid formulations which contain 601 mg to 6 g, in particular 610 mg to 2 g, preferably 650 mg to 1 g of dihydrolipoic acid or a pharmaceutically acceptable salt thereof, or in the form of solutions, suspensions or emulsions which contain 182 mg/ml to 1137 mg/ml, preferably 200 mg/ml to 1000 mg/ml, in particular 300 mg/ml to 500 mg/ml of dihydrolipoic acid or a pharmaceutically acceptable salt thereof.

D. Pharmaceutical compositions according to one or several of the above mentioned agents according to A) to C) which contain at least one compound of Formula I and which also contain conventional pharmaceutical carriers, auxiliary substances, stabilizers, solubilizers and/or diluents. In the case of solutions, additional stabilizers and/or solubilizers may also be present. Stabilizers or solubilizers that may for example be used are: aliphatic $C_2$-$C_4$-alcohols containing one, two or three hydroxyl groups, polyethylene glycols of molecular weights between 200–600; conventional physiologically acceptable organic amides, natural α-amino acids, aliphatic amines, hydroxyethyl theophylline, tromethamine, diethylene glycol monomethyl ether.

E. A process for the preparation of a pharmaceutical composition which contains at least one compound of the aforesaid Formula I, where X is a hydrogen atom or both X represent a simple bond between the two sulphur atoms; Y is hydrogen or $C_1$-$C_6$-alkyl and n represents a number from 1 to 10 or their therapeutically acceptable salts with the exception of α-lipoic acid and dihydrolipoic acid along with conventional pharmaceutical carriers and/or diluents or other auxiliary substances which comprises processing into pharmaceutical formulations or bringing into a therapeutically acceptable form.

F. A process for the preparation of a pharmaceutical composition which contains at least one compound of the aforesaid Formula I, where X is a hydrogen atom or both X's represent a direct link between the two sulphur atoms; Y is hydrogen or $C_1$-$C_6$-alkyl and n represents a number from 1 to 10 their therapeutically acceptable salts with the exception of α-lipoic acid and dihydrolipoic acid is processed with conventional pharmaceutical carrier substances and/or diluting agents or other auxiliary substances into pharmaceutical formulations or brought into a therapeutically applicable form, the dosage unit for solid or semi-solid formulations containing 20 mg to 6 g, preferably 50 mg to 2 g, in particular 100 mg to 1 g or also 400 mg or 500 mg to 1 g of the total amount of the active substance of Formula I, or solutions, suspensions or emulsions which contain 0.2 mg to 800 mg per ml, in particular 10 mg to 500 mg, preferably 40 mg to 200 mg per ml of the total amount of active substance I or a pharmaceutically acceptable salt thereof.

G. A process for the preparation of a pharmaceutical composition in which α-lipoic acid or dihydrolipoic acid is processed into pharmaceutical formulations or brought into a therapeutically acceptable form with conventional pharmaceutical carrier substances and/or diluting agents or other auxiliary substances, the dosage unit for solid or semi-solid formulations in the case of the α-lipoic acid containing 51 mg to 6 g, preferably 100 mg to 2 g, in particular 200 mg to 1 g or also 400 mg or 500 mg to 1 g of α-lipoic acid or a pharmaceutically acceptable salt thereof or, in the case of the α-lipoic acid, injection solutions that contain 26 mg to 500 mg per ml, preferably 50 mg to 200 mg, in particular 100 mg per ml of α-lipoic acid or a pharmaceutically acceptable salt thereof, or drinkable solutions, suspensions or emulsions which contain 0.2 mg to 500 mg per ml, preferably 1 mg to 50 mg per ml, in particular 5 mg to 10 mg per ml of α-lipoic acid or a pharmaceutically acceptable salt thereof, the dosage unit for solid or semi-solid formulations in the case of the dihydrolipoic acid containing 601 mg to 6 g, in particular 610 mg to 2 g, preferably 650 mg to 1 g of dihydrolipoic acid or a pharmaceutically acceptable salt thereof or solutions, suspensions or emulsions which contain 182 mg/ml to 1137 mg/ml, preferably 200 mg/ml to 1000 mg/ml, in particular 300 mg/ml to 500 mg/ml of dihydrolipoic acid or a pharmaceutically acceptable salt thereof.

H. A process for the preparation of a pharmaceutical composition in which a compound of Formula I or a phamaceutically acceptable salt thereof is mixed with one or several of the following substances: starch, cyclodextrin, urea, cellulose, cellulose derivatives, lactose, formalin-casein, modified starch, magnesium stearate, calcium hydrogen phosphate, silica gel, talcum. The mixture obtained is granulated or pelleted optionally with an aqueous or alcoholic solution which may contain gelatin, starch, pollyvinyl pyrrolidone, vinyl pyrrolidone-, vinyl acetate-copolymerizate and/or polyoxyethylene sorbitan monooleate as a component. The resulting granulate or pellets are homogenized optionally with one or several of the above named auxiliary substances and then pressed into tablets or filled into capsules or the granulate or the pellets are filled into bags, the tablets, capsules or bags in the dosage unit
  a) in the case of compounds of Formula I with the exception of α-lipoic acid and dihydrolipoic acid, containing 20 mg to 6 g, in particular 50 mg to 2 g, preferably 100 mg to 1 g of the total amount of active substance I or of a salt thereof;
  b) in the case of α-lipoic acid, containing 51 mg to 6 g, in particular 100 mg to 2 g, preferably 200 mg to 1 g or also 400 mg or 500 mg to 1 g of α-lipoic acid or a salt thereof;
  c) in the case of dihydrolipoic acid, containing 601 mg to 6 g, in particular 610 mg to 2 g, preferably 650 mg to 1 g of dihydrolipoic acid or a salt thereof.

I. A process for the preparation of a pharmaceutical composition in which a compound of Formula I or a pharmaceutically acceptable salt thereof is homogenized and/or emulsified into a mixture at a temperature between 20° and 120° C., optionally in the presence or one and/or several emulsifiers and/or complex formers with at least one of the following substances: water, glycerol, paraffin, Vaseline, aliphatic alcohol with 12 to 25 carbon atoms, aliphatic monocarboxylic acid with 15 to 20 carbon atoms, sorbitan monopalmitate, polyoxyethylene polyol fatty acid ester, mono- or multivalent low molecular aliphatic alcohol, fatty acid glyceride, wax, silicon, polyethylene glycol, a mixture of this type representing a brushable formulation and
  a) in the case of compounds of Formula I with the exception of dihydrolipoic acid, containing 0.1 to 50% by weight, in particular 0.5 to 20, preferably 1 to 10% by weight of the total amount of active substance I (including α-lipoic acid) or of a salt thereof;
  b) in the case of dihydrolipoic acid, containing 21 to 99, in particular 25 to 70, preferably 30 to 40% by weight of dihydrolipoic acid or a salt thereof.

J. A process for the preparation of a pharmaceutical composition in which a compound of Formula I or a pharmaceutically acceptable salt thereof is dissolved at temperatures between 20° and 100° C., optionally in the presence of a complex former and/or of an emulsifier in water, physiologically acceptable alcohols, dimethyl sulphoxide, polyethylene oxide or oils or mixtures thereof and optionally the solution so obtained is diluted with sufficient water, alcohol, dimethyl sulphoxide, polyethylene oxide or oil that the final solution, final suspension or final emulsion
  a) in the case of compounds of Formula I with the exception of α-lipoic acid and dihydrolipoic acid contains 0.2 mg to 800 mg per ml, in particular 10 mg to 500 mg, preferably 40 mg to 200 mg per ml of the total amount of active substance I or of a salt thereof;
  b) in the case of injection solutions of α-lipoic acid, contains 26 mg to 500 mg per ml, in particular 50 mg to 200 mg, preferably 100 mg per ml α-lipoic acid or of a salt thereof;
  c) in the case of drinkable solutions, suspensions or emulsions of α-lipoic acid, contains 0.2 mg to 500 mg per ml, preferably 1 mg to 50 mg per ml, in particular 5 mg to 10 mg per ml α-lipoic acid or a pharmaceutically acceptable salt thereof;
  d) in the case of dihydrolipoic acid, contains 182 mg/ml to 1137 mg/ml, preferably 200 mg/ml to 1000 mg/ml, in particular 300 mg/ml to 500 mg/ml of dihydrolipoic acid or a pharmaceutically acceptable salt thereof.

K. A process for the preparation of a pharmaceutical composition in which the preparation of these pharmaceutical compositions which contain as active substance at least one compound of Formula I is in addition carried out with added conventional stabilizers and/or solubilizers.

L. A process for the preparation of a pharmaceutical composition in which the following substances are added during preparation as stabilizers or solubilizers: aliphatic $C_2$–$C_4$-alcohols that contain one, two or three hydroxyl groups, polyethylene glycols with molecular weights between 200–600; conventional physiologically acceptable organic amides, natural α-amino acids, aliphatic amines, hydroxyethyl theophylline, tromethamine, diethylene glycol monomethyl ether.

M. The method of treating disorders, for example those caused by retroviruses, which comprises administering an effective amount of one of the foregoing pharmaceutical compositions.

The appropriate pharmaceutical compositions may also be used in mixture with other pharmacologically active substances. In particular the active substances of Formula I may also be combined with other agents active against retroviruses, in particular HIV, for example with didesoxyinosin, didesoxycytidine, but in particular with α-interferon and/or azidothymidine (AZT).

The pharmaceutical compositions according to the invention may also contain in each case as active substance a single compound of Formula I or two or more compounds of Formula I. In the latter case the dosages given always relate to the sum of the active ingredients according to Formula I, that is the active component I or component a. The same also applies in the case of combinations, for example combinations with other antiretrovirally active substances (component b). Here, too, it is possible only to use one, but also two and more (preferably two) antiretrovirally active ingredients as component b, in the latter case the dosages quoted here always apply to the sum of the antiretrovirally active substances present in each case. The term "dosage unit" always relates to a single dose that may also be given several times a day.

If the dose is quoted in the form of enzyme units, this is the dose which applies for an entire day, such a dose being given once or, however, preferably divided over the day (for example in the form of an infusion). The dosage quoted in enzyme units applies in particular to combinations with α-interferon.

The invention also relates to the use of compounds of the aforesaid Formula I where X is a hydrogen atom or both X represent a direct link between the two sulphur atoms; Y is hydrogen or $C_1$-$C_6$-alkyl and n represents a number from 1 to 10, or therapeutically acceptable salts thereof for combating retroviruses, in particular human immunodeficiency virus (HIV) as well as agents for treating disorders caused by retroviruses which contain compounds of Formula I or their therapeutically acceptable salts as active substances.

Pharmaceutical compositions of this type may contain conventional pharmaceutical carrier, auxiliary and/or diluting agents. The invention therefore also relates to a process for formulating active ingredients of Formula I with conventional pharmaceutical carrier, auxiliary and/or diluting agents into a pharmaceutical composition for the treatment of disorders caused by retroviruses.

The agents for combating retroviruses contain the active ingredients of Formula I for example in such amounts that an active ingredient level of between 3.5 and 200 mg/kg body weight is present in the body with administration once or several times daily.

The present invention also relates to a product for combating retroviruses which is characterized in that it contains in addition to the conventional pharmaceutical carrier and/or diluting or auxiliary substances
  a) a compound of the aforesaid Formula I where X is a hydrogen atom or both X represent a direct link between the two sulphur atoms; Y is hydrogen or $C_1$-$C_6$-alkyl and n represents a number from 1 to 10 and
  b) another antiretrovirally active ingredient
or in each case a physiologically acceptable salt of both active substances in an amount generating a synergistic effect and present in a form which permits both joint and also separate therapeutic use of both active substances.

The other substance active against retroviruses may for example be: azidothymidine (AZT), didesoxyinosin (DDI), α-interferon or didesoxycytidine (DDC).

In the above mentioned product contains, for each part by weight of a compound of Formula I (active component I or component a) 0.01 to 100 parts by weight of the other component b), or each mg of active component I (component a) is combined with 20–200,000 enzyme units of the other component b), or that, in the dosage unit, the combination contains 50 mg to 6 g, preferably 200 mg to 2 g of active component I and 10 to 300 mg, preferably 50 to 200 mg or $5 \times 10^5$ enzyme units to $8 \times 10^6$ enzyme units, preferably $1 \times 10^6$ to $4 \times 10^6$ enzyme units of the other component b).

In addition, an agent/product of this type may also contain vitamins, preferably vitamins $B_1$ and/or E.

The invention also relates to a process for preparing one of the above described products in which 1 part by weight of active component of Formula I and 0.01 to 100 parts by weight or 20 to 200,000 enzyme units of the other component b), where the active substances may also be present in the form of its salt, is processed together with conventional carrier and/or diluting or auxiliary substances as well as optionally with addition of vitamins into products which contain, in each dosage unit, 50 mg to 6 g of active component I and 10 to 300 mg or $5 \times 10^5$ to $8 \times 10^6$ enzyme units of the other component b).

The compounds of Formula I including α-lipoic acid and dihydrolipoic acid may also be used in the form of their optical isomeric (R(+) and S-(−) form, compounds of Formula I conventionally being present as racemates) or diastereomeric forms for the preparation of pharmaceutical compositions and formulations and for the cited use. The compounds of Formula I are preferably α-lipoic acid and dihydrolipoic acid (racemates as well as the corresponding enantiomers).

α-lipoic acid is widely available in the form of the racemate (Thioctsäure$^R$) in plants and animals; it acts as co-enzyme in many enzymatic reactions, constitutes a growth factor for certain bacteria and protozoas and is used in death-head fungus poisoning. In addition, the α-lipoic acid racemate displays anti-inflammatory, antinociceptive (analgesic) and cytoprotective properties.

Thioctacid is marketed as a pharmaceutical composition for the following indications: adiposis hepatica, fatty cirrhosis, in particular chronic liver disorders due to alcohol, liver damage caused by mushroom poisoning, diabetic neuropathy, alcoholic neuropathy.

Dihydrolipoic acid is 6,8-dimercapto-octanoic acid. It is known from animal experiments that dihydrolipoic acid inactivates snake venom. These investigations have for example been carried out in rats and mice, solutions in water or physiological salt solution being used which contained the snake venom and dihydrolipoic acid.

In the hitherto used formulations, the α-lipoic acid and dihydrolipoic acid are present in relatively small amounts.

The pharmaceutical compositions of the invention which contain larger amounts of α-lipoic acid and dihydrolipoic acid are novel; moreover the fact that higher dosages of these active substances display more advantageous pharmaceutical effects, for example in the treatment of AIDS, was not obvious.

The preparation of the pharmaceutical compositions of the invention is carried out in known manner, it being possible to use known and conventional pharmaceutical auxiliary substances as well as other conventional carrier and diluting agents. Carrier and diluting agents that may for example be used are those recommended and/or quoted in the following literature reference as being auxiliary substances for pharmacy, cosmetics and related fields: Ullmanns Enzyklopädie der technischen Chemie, Volume 4 (1953), page 1 to 39; Journal of Pharmaceutical Sciences, Volume 52 (1963), page 918 et seq., H. v. Czetsch-Lindenwald, Hilfsstoffe für Pharmazie und angrenzende Gebiete; Pharm. Ind., Issue 2 (1961), page 72 et seq.; Dr. H.P. Fiedler, Lexikon der Hilfsstoffe für Pharmazie, Kosmetik und angrenzende Gebiete, Cantor KG, Aulendorf in Württemberg (1989). .

The pharmaceutical and galenic handling of the compounds of Formula I is effected using conventional standard methods. For example the active ingredients and auxiliary or carrier substances are well mixed by stirring or homogenizing (for example using conventional mixing apparatus) working generally being at temperatures between 20° and 50° C., preferably 20° and 40° C., in particular at room temperature. In addition, reference is made to the following standard work: Sucker, Fuchs, Speiser, Pharmazeutische Technologie, Thieme-Verlag Stuttgart, 1978.

The pharmaceutical compositions may be applied to the skin or mucous membranes or to the inside of the body, application for example being oral, enteral, pulmonal, nasal, lingual, intravenous, intra-arterial, intracardial, intramuscular, intraperitoneal, intracutaneous, subcutaneous.

The parenteral forms of application are in particular sterile or sterilized products.

The compounds of Formula I may also be used in the form of their therapeutically acceptable salts. These salts may be prepared in the conventional manner.

Salt formers that may for example be used are conventional bases or cations which are physiologically acceptable in the salt form. Examples thereof are: alkali metals or alkaline earth metals, ammonium hydroxide, basic amino acids such as arginine and lysine, amines of formula $NR_1R_2R_3$ where the radicals $R_1$, $R_2$ and $R_3$ are the same or different and represent hydrogen, $C_1$–$C_4$-alkyl or $C_1$–$C_4$-oxyalkyl such as mono- and diethanolamine, 1-amino-2-propanol, 3-amino-1-propanol; alkylene diamines having one alkylene chain composed of 2 to 6 carbon atoms such as ethylene diamine or hexamethylene tetramine, saturated cyclic amino compounds with 4–6 cyclic carbon atoms such as piperidine, piperazine, pyrrolidine, morpholine; N-methyl glucamine, creatine, tromethamine.

Should the compounds of Formula I be used in the form of their salts, the salt former may also be used in excess, i.e. in an amount greater than equimolar.

Examples of carrier and auxiliary substances are gelatin, natural sugars such as raw sugar or lactose, lecithin, pectin, starches (for example corn starch or amylose), cyclodextrins and cyclodextrin derivatives, dextran, polyvinyl pyrrolidone, polyvinyl acetate, gum arabic, alginic acid, tylose, talcum, lycopodium, silica gel (for example colloidal), cellulose, cellulose derivatives (for example cellulose ethers in which the cellulose hydroxy groups are partially etherified with lower saturated aliphatic alcohols and/or lower saturated aliphatic oxyalcohols, for example methyl·oxypropyl cellulose, methyl cellulose, hydroxypropyl methyl cellulose, hydroxypropyl methyl cellulose phthalate); fatty acids as well as magnesium, calcium or aluminum salts of fatty acids with 12 to 22 carbon atoms, in particular saturated (for example stearates), emulsifiers, oils and fats, in particular vegetable (for example, peanut oil, castor oil, olive oil, sesame oil, cottonseed oil, corn oil, wheat germ oil, sunflower seed oil, cod liver oil, in each case also hydrated); glycerol esters and polyglycerol esters of saturated fatty acids $C_{12}H_{24}O_2$ to $C_{18}H_{36}O_2$ and their mixtures, it being possible for the glycerol hydroxy groups to be totally or also only partly esterified (for example mono-, di- and triglycerides); pharmaceutically acceptable mono- or multivalent alcohols and polyglycols such as polyethylene glycol and derivatives thereof, esters of aliphatic saturated or unsaturated fatty acids (2 to 22 carbon atoms, in particular 10–18 carbon atoms) with monovalent aliphatic alcohols (1 to 20 carbon atoms) or multivalent alcohols such as glycols, glycerol, diethylene glycol, pentaerythritol, sorbitol, mannitol and the like, which may optionally also be etherified, esters of citric acid with primary alcohols, acetic acid, urea, benzyl benzoate, dioxolanes, glyceroformals, tetrahydrofurfuryl alcohol, polyglycol ethers with $C_1$–$C_{12}$-alcohols, dimethylacetamide, lactamides, lactates, ethylcarbonates, silicones (in particular medium-viscous polydimethyl siloxanes), calcium carbonate, sodium carbonate, calcium phosphate, sodium phosphate, magnesium carbonate and the like.

Other auxiliary substances that may be considered are those which cause disintegration (so-called disintegrants), such as: cross-linked polyvinyl pyrrolidone, sodium carboxymethyl starch, sodium carboxymethyl cellulose or microcrystalline cellulose. Conventional coating substances may also be used. Those that may for example be considered are: polymerizates as well as copolymerizates of acrylic acid and/or methacrylic acid and/or their esters; copolymerizates of acrylic and methacrylic acid esters with a lower antmonium group content (for example Eudragit$^R$ RS), copolymerizates of acrylic and methacrylic acid esters and trimethyl ammonium methacrylate (for example Eudragit$^R$ RL); polyvinyl acetate; fats, oils, waxes, fatty alcohols; hydroxypropyl methyl cellulose phthalate or -acetate succinate; cellulose acetate phthalate, starch acetate phthalate as well as polyvinyl acetate phthalate; carboxy methyl cellulose; methyl cellulose phthalate, methyl cellulose succinate, -phthalate succinate as well as methyl cellulose phthalic acid half ester; zein; ethyl cellulose as well as ethyl cellulose succinate; shellac, gluten; ethylcarboxyethyl cellulose; ethacrylate-maleic acid anhydride copolymer; maleic acid anhydride-vinyl methyl ether copolymer; styrol-maleic acid copolymerizate; 2-ethyl-hexyl-acrylate maleic acid anhydride; crotonic acid-vinyl acetate copolymer; glutaminic acid/glutamic acid ester copolymer; carboxymethylethylcellulose glycerol monooctanoate; cellulose acetate succinate; polyarginin.

Plasticizing agents that may be considered as coating substances are: Citric and tartaric acid esters (acetyl-triethyl citrate, acetyl tributyl-, tributyl-, triethylcitrate); glycerol and glycerol esters (glycerol diacetate, - triacetate, acetylated monoglycerides, castor oil); phthalic acid esters (dibutyl-, diamyl-, diethyl-, dimethyl-, dipropyl-phthalate), di-(2-methoxy- or 2-ethoxyethyl)-phthalate, ethylphthalyl glycolate, butylphthalylethyl glycolate and butylglycolate; alcohols (propylene glycol, polyethylene glycol of various chain lengths), adipates (diethyladipate, di-(2-methoxy- or 2-ethoxyethyl)-adipate; benzophenone; diethyl- and dibutylsebacate, dibutylsuccinate, dibutyltartrate; diethylene glycol dipropionate; ethyleneglycol diacetate, -dibutyrate, -dipropionate; tributyl phosphate, tributyrin; polyethylene glycol sorbitan monooleate (polysorbates such as Polysorbat 80); sorbitan monooleate.

For the preparation of solutions or suspensions it is for example possible to use water or physiologically acceptable organic solvents, such as alcohols (ethanol, propanol, isopropanol, 1,2-propylene glycol, polyglycols and their derivatives, fatty alcohols, partial esters of glycerol), oils (for example peanut oil, olive oil, sesame oil, almond oil, sunflower oil, soya bean oil, castor oil, bovine hoof oil), paraffins, dimethyl sulphoxide, triglycerides and the like.

In the case of injectable solutions or suspensions it is for example possible to use non-toxic parenterally acceptable diluting agents or solvents, such as: water, 1,3-butane diol, ethanol, 1,2-propylene glycol, polyglycols mixed with water, glycerol, Ringer's solution, isotonic salt solution or also hardened oils including synthetic mono or diglycerides or fatty acids such as oleic acid.

In preparing the formulations it is possible to use known and conventional solubilizers or emulsifiers. Solubilizers and emulsifiers that may for example be used are: polyvinyl pyrrolidone, sorbitan fatty acid esters such as sorbitan trioleate, phosphatides such as lecithin, acacia, tragacanth, polyoxyethylated sorbitan monooleate and other ethoxylated fatty acid esters of sorbitan, polyoxyethylated fats, polyoxyethylated oleotriglycerides, linolizated oleotriglycerides, polyethylene oxide condensation products of fatty alcohols, alkylphenols or fatty acids or also 1-methyl-3-(2-hydroxyethyl)imidazolidone-(2). In this context, polyoxyethylated means that the substances in question contain polyoxyethylene chains, the degree of polymerization of which generally lies between 2 and 40 and in particular between 10 and 20.

Polyoxyethylated substances of this kind may for example be obtained by reaction of hydroxyl group-containing compounds (for example mono- or diglycerides or unsaturated compounds such as those containing oleic acid radicals) with ethylene oxide (for example 40 Mol ethylene oxide per 1 Mol glyceride).

Examples of oleotriglycerides are olive oil, peanut oil, castor oil, sesame oil, cottonseed oil, corn oil. See also Dr. H.P. Fiedler "Lexikon der Hilfsstoffe für Pharmazie, Kosmetik und angrenzende Gebiete" 1971, pages 191-195.

In the case of aqueous injection and drinkable solutions the following substances are in particular used as stabilizers or solubilizers: lower aliphatic mono- and multivalent alcohols with 2–4 carbon atoms, such as ethanol, n-propanol, glycerol, polyethylene glycols with molecular weights between 200-600 (for example 1 to 40% aqueous solution), diethylene glycol monoethyl ether, 1,2-propylene glycol, organic amides, for example amides of aliphatic $C_1$-$C_6$-carboxylic acids with ammonia or primary, secondary or tertiary $C_1$-$C_4$-amines or $C_1$-$C_4$-hydroxy amines such as urea, urethane, acetamide, N-methyl acetamide, N,N-diethyl acetamide, N,N-dimethyl acetamide, lower aliphatic amines and diamines with 2-6 carbon atoms, such as ethylene diamine, hydroxyethyl theophylline, tromethamine (for example as 0.1 to 20% aqueous solution), aliphatic amino acids. The amino acids are for example amino acids having the following structure:

$$R'-CH-CO_2H$$
$$|$$
$$NH_2$$

where R' represents hydrogen, a phenyl radical, an indolyl-(3)-methyl radical, imidazolyl-(4)-methyl radical, a $C_1$-$C_{10}$-alkyl group or a $C_1$-$C_{10}$ alkyl group which is substituted by a hydroxy group, a carboxy group, a $C_1$-$C_6$-alkoxy group, a mercapto group, a $C_1$-$C_6$-alkylthio group, an amino group, a phenyl group, a hydroxyphenyl group, a $C_2$-$C_6$-alkanoylamino group or a $C_1$-$C_6$-alkoxycarbonyl group.

The following formulations may for example be considered for drinkable or injection solutions:

| | |
|---|---|
| α-lipoic acid | 10% |
| L-lysine | 7.66% |
| ethylene diamine | 0.27% |
| water | 82.07% |
| α-lipoic acid | 10% |
| L-lysine | 7.66% |
| tromethamine | 1% |
| water | 81.34% |
| dihydrolipoic acid | 1% |
| tromethamine | 0.9% |
| ethylene diamine | 0.38% |
| water | 97.72% |
| dihydrolipoic acid | 1% |
| tromethamine | 1.5% |

| -continued | |
|---|---|
| 1,2-propylene glycol | 20% |
| nicotinic acid amide | 10% |
| water | 67.5% |

It is also possible to add preservatives, stabilizers, buffer substances, flavor correcting agents, sweeteners, colorants, antioxidants and complex formers and the like. Complex formers which may be for example be considered are: chelate formers such as ethylene diamine tetraacetic acid, nitrilotriacetic acid, diethylene triamino pentaacetic acid and their salts.

The complex formers used may also be those enclosing the R- or S- α-lipoic acid in a hollow space. Examples thereof are urea, thiourea, cyclodextrines, amylose.

It may optionally be necessary to stabilize the active substance molecule with physiologically acceptable bases or buffers to a pH range of ca. 6 to 9. Preference is generally given to as neutral or weakly basic a pH value as possible (up to pH 8).

Antioxidants that may for example be used are sodium sulphite, sodium hydrogen sulphite, sodium metabisulphite, ascorbic acid, ascorbylpalmitate, -myristate, -stearate, gallic acid, gallic acid alkyl ester, butylhydroxyanisol, nordihydroguaiacic acid, tocopherols as well as synergists (substances which bind heavy metals through complex formation, for example lecithin, ascorbic acid, phosphoric acid ethylene diamine tetraacetic acid, citrates, tartrates). Addition of synergists substantially increases the antioxygenic effect of the antioxidants.

Preservatives that may for example be considered are sorbic acid, p-hydroxybenzoic acid esters (for example lower alkyl esters), benzoic acid, sodium benzoate, trichloroisobutyl alcohol, phenol, cresol, benzethonium chloride, chlorhexidine and formalin derivatives.

The compounds of the present invention of general Formula I also have in particular a growth-inhibiting effect against retroviruses, in particular human iramunodeficiency virus (HIV, for example HIV-1. HIV-2) and an activating and growth-promoting effect on peripheral mononuclear blood cells. For example the compounds I retard or inhibit proliferation of the virus.

Retroviruses against which the compounds/products of the invention are effective are for example: HIV viruses, oncorna viruses, spuma viruses.

For example the compounds of Formula I have a good, growth-inhibiting effect on HIV (type 1 and 2) which may be shown in vitro for example in the following virological-cell biological test processes:

1. Plaque reduction test
2. CPE reduction test
3. Determination of reverse transcriptase in culture supernatant
4. Determination of the p24 antigen in culture supernatant Thus, for example, a single dose of 0.035 mg/ml of compound I (for example alpha-lipoic acid, racemate) reduces the number of infectious viruses (for example HIV-1) in cell culture supernatant from 100% in the positive control to 0%. In this test procedure a virus-inhibiting effect can be demonstrated even in very low doses, for example 0.001 mg/ml.

The general dosage range for the effect (experiment as above) is for example: 0.0035-0.091 mg/ml, in particular 0.035-0.070 mg/ml.

For the in vitro trials the active substance of Formula I is used, for example in benzyl alcohol as solvent.

For in vitro investigations into the replication behavior of retroviruses, in particular HIV, it is for example possible to use the following substrates:

1. Virus-containing RPMI 1640 medium, for example 1X liquid 041-01875 (synthetic culture medium from Gibeo according to Moore, Gerner and Franklin, H.A. (1967), J.A.M.A. 199; 519) with a concentration of $2 \times 10^3 - 1 \times 10^4$ infectious units (PFU)/ml.
2. The cell lines Jurkat Clone E6-1, Sup T1 and HeLa CT4.

Cell line Jurkat Clone E6-1

Cell type: human T-cell leukemia. Growth medium: RPMI 1640, 90%; fetal calf serum, 10%. Freezing medium: culture medium, 90%; dimethyl sulphoxide, 10%. Proportion of living cells: 80%. Growth characteristics: the cells are passaged every 2 to 3 days. The cell count should be kept between $10^5$ and $10^6$ cells/ml. Morphology: lymphocytary. Caryology: not stated. Sterility: bacteria and mycoplasmas negative. Reverse transcriptase: negative. Special characteristics: this clone of Jurkat-FHCRC (Dr. Kendall Smith, Dartmouth) produces large amounts of interleucin-2 (IL-2) after appropriate stimulation. The cells may be induced to secrete gamma interferon and are CH4+. Source: ATCC from Dr. Arthur Weiss. References: Journal of Immunology, 133:123, 1984.

Cell line Sup-T1

Cell type: non-Hodgkin's T-cell lymphoma. Growth medium: McCoy's 5A medium, 85%; fetal calf serum, 15%. The cells grow on a feeder layer (complete medium with 10% normal human serum and 0.5% agar). Freezing medium, 90%; dimethyl sulphoxide, 10%. Proportion of living cells: 80%. Growth characteristics: the cells are passaged when the cell concentration becomes greater than $5 \times 10^5$/ml. For the passage the culture is diluted 1:10 to 1:20 with fresh growth medium. Morphology: matured lymphocytary. Caryology: not stated. Sterility: bacteria and mycoplasmas negative. Reverse transcriptase: negative. Special characteristics: the cells are TdT positive, CALLA negative, DR negative. They express pan T-antigens, have no sheep erythrocyte receptor and express high levels of surface-CD4. Source: Dr. James Hoxie, references: Cancer Research 44:5657, 1984.

3) Cell line HeLa T4+

Cell type: human epithelium-like. Growth medium: culture medium consisting of various amino acids and electrolytes for the cultivation of epithelial cells (for example Dulbecco's minimal essential medium, DME), 90%; serum of newborn calves, 10%. Freezing medium: culture medium, 95%; glycerol, 5%, without antibiotics. Proportion of living cells, 80%. Growth characteristics similar to the line of origin. Morphology: similar to the line of origin. Caryology: not stated. Sterility: bacteria and mycoplasmas negative. Reverse transcriptase: negative. Special properties: prior to the retrovirus-mediated gene transfer with CD4cDNA these cells do not express any surface CD4 and are not sensitive to the AIDS virus infection. After transfection, CD4+ cells permit infection by the AIDS virus and the induction of syncytes. Source: Dr. Richard Axel. References: Cell 47:333, 1986.

FURTHER INFORMATION ON HIV REPLICATION BY α-LIPOIC ACID IN VITRO

The inhibitory effect is shown in a cell line permanently infected with HIV-1.

Preparation of a cell line permanently infected with HIV-1

1. Negative (non infected) cells (for example Molt 4) are removed from the culture bottle with RPMI 1640 culture medium and centrifuged down in an appropriate vessel. As a basic principle, the negative cells may be the cells from any CD4 receptor-positive T-cell line. It is, for example, possible to use the following commercially available cell lines: H9, Hut78, SupT1, Jurkat, Molt4. Molt4 is for example a monoclonal T-cell line of the peripheral blood of a cancer patient. T-cell lines are derived from human tumors, for example from specific forms of leukemia. Cell lines of this type grow permanently as long as they are kept in the appropriate culture medium and $CO_2$ concentration in an incubator at 37° C. These lines may be purchased from the American Type Culture Collection (ATCC).
2. These Molt4 cells are then resuspended (taken up) in highly virus-containing culture medium (RPMI 1640+10% fetal calf serum) placed in a culture flask and incubated (cultivated) for ca. 12 hours in an incubator at 37° C. and 5% $CO_2$. This infects part (depending on the concentration of the infectious virus) of the cells.
3. After 12 hours the cells are again separated by centrifugation and resuspended in fresh medium (RPMI 1640, containing no virus) and cultivated for ca. 4 weeks in an incubator.
4. Once every week the medium is completely replaced (separated by centrifugation, resuspended, etc.) and negative, non-infected cells are added.
5. After ca. 4 weeks 80-100% of the cells are infected=permanently infected cell line. The infection is for example determined using immunofluorescence. The cells infected in this manner produce HIV in a titer range of about $10^5-10^6$ infectious units (PFU). The tumor cell line permanently infected in this manner (Molt4) is treated for three weeks with 70 μg of α-lipoic acid/ml. Every three days culture medium and α-lipoic acid are replaced and the activity of the virus determined in the reverse transcriptase and plaque test. The reverse transcriptase test determines the relative amount of virus formed (also in infection-defective particles) whereas the plaque test is only able to determine infectious virus units.

The concentration range selected of 70 μg/ml is about 10-20 times above the plasma levels measured with normal, oral, side effect-free dosage. The proliferation rate or lethality of peripheral blood lymphocytes is not substantially affected by this dosage.

Figure 1:
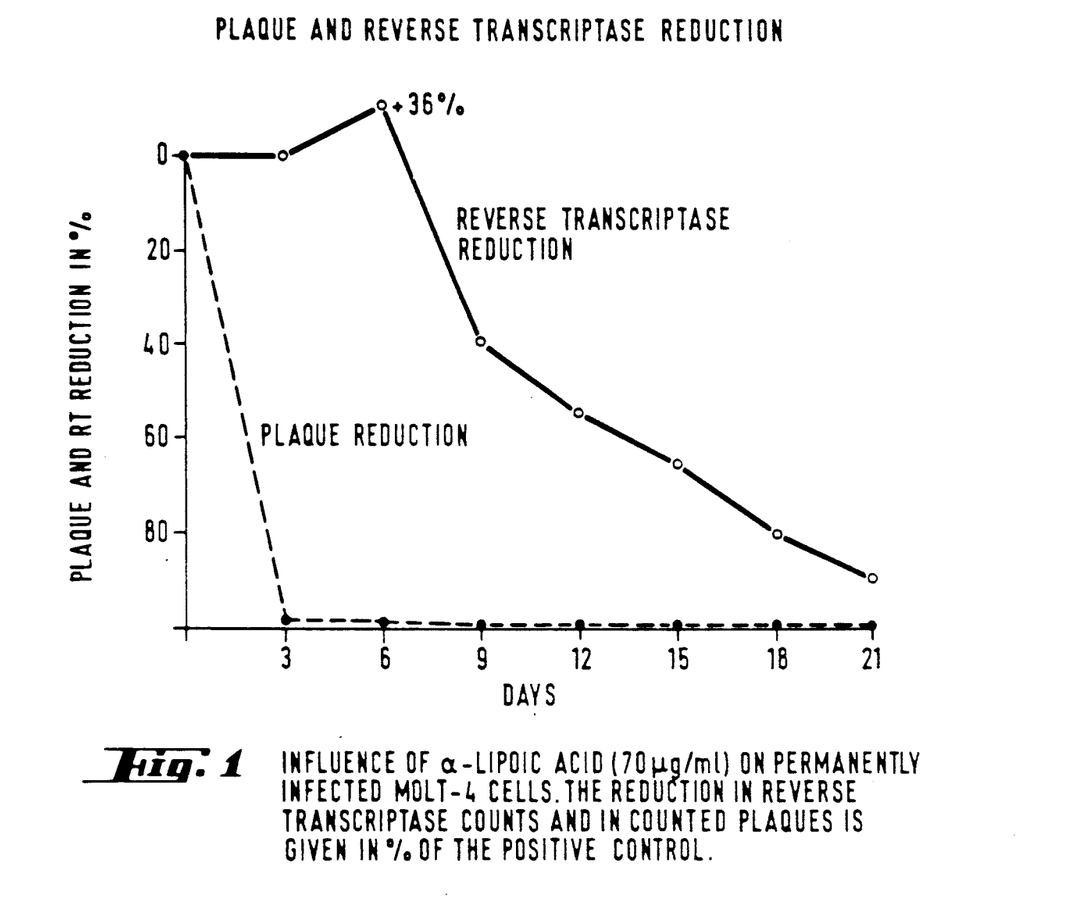
FIG. 1 is a graph showing reductions in plaque count and reverse transcriptase count caused by α-lipoic acid, as a function of time.

As shown by the curves in FIG. 1, the number of infectious virus units falls after only 3 days to about 0, corresponding to an almost 100% reduction. The number of virus units produced only falls as from day 6 and reaches a reduction of 90% after three weeks. These results demonstrate the great antiviral potency of α-lipoic acid. The second important result worthy of recording is that there is no sign or evidence of the development of tolerance after three weeks in a concentration range of 70 μg/ml. This is of particular importance in the long-term treatment of infected persons.

Figure 2:
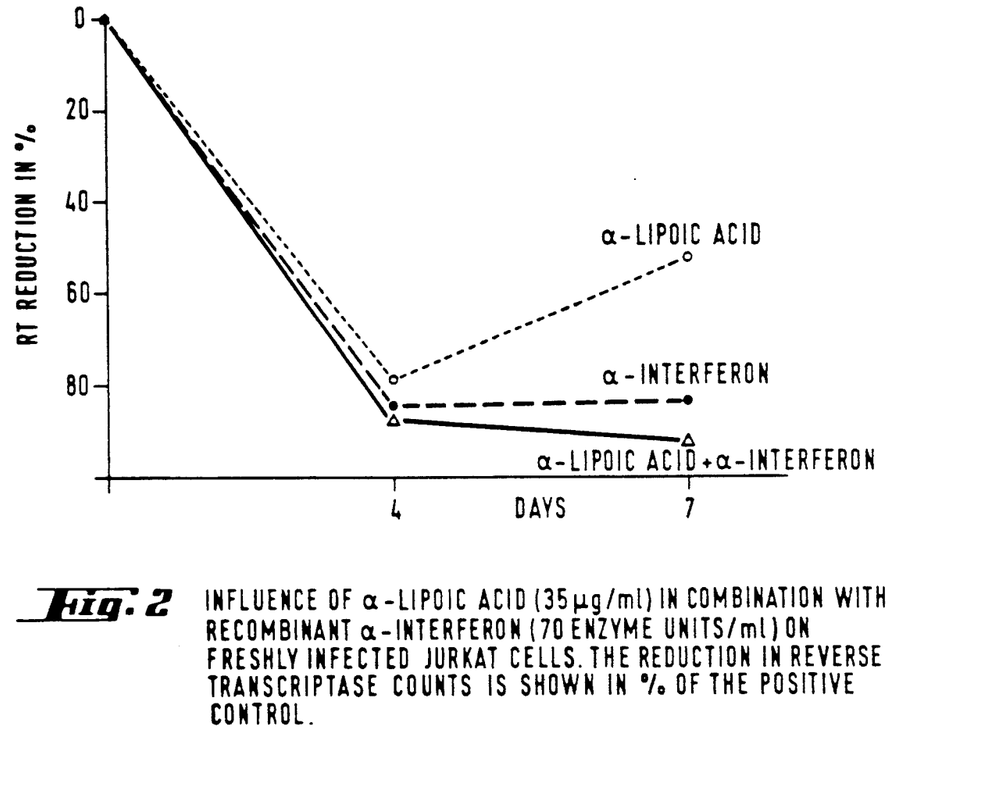
FIG. 2 is a graph showing reductions in reverse transcriptase count caused by α-lipoic acid, recombinant α-interferon and a combination of α-lipoic acid and recombinant α-interferon.
Figure 3:
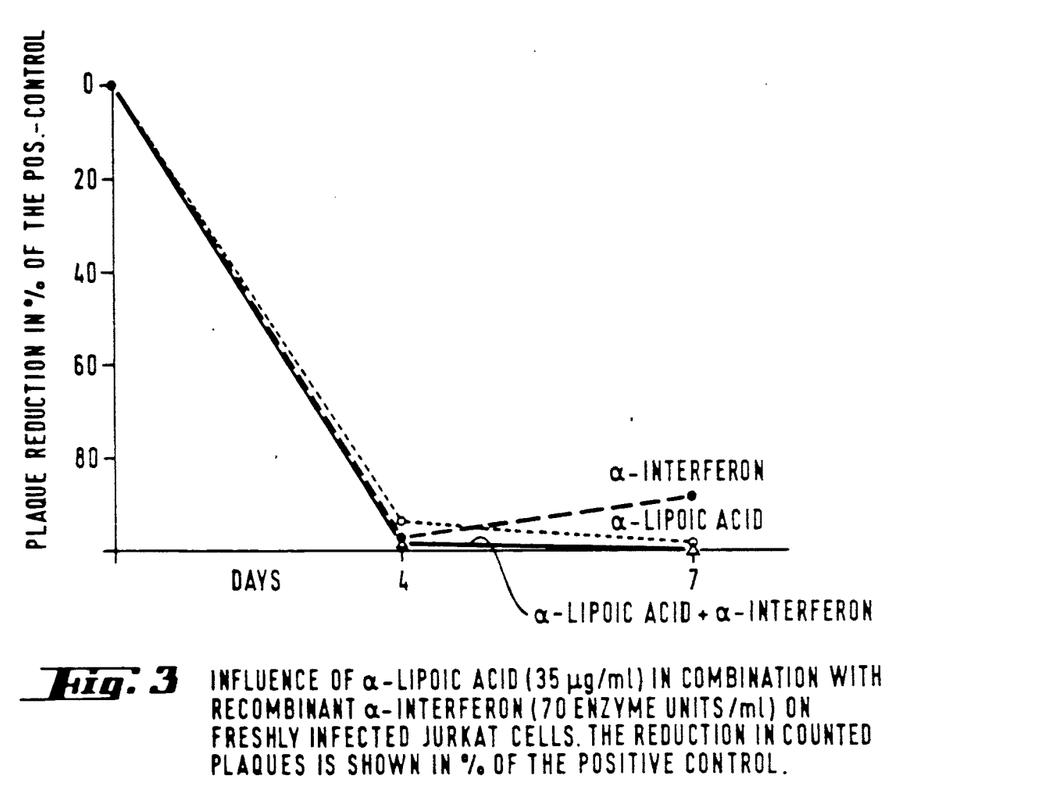
FIG. 3 is a graph showing reductions in plaque count caused by α-lipoic acid, recombinant α-interferon and a combination of α-lipoic acid and α-interferon.

Should one wish to compare the in vitro effect of α-lipoic acid with other agents which have already been successfully used in the treatment of AIDS, alpha interferon may be considered. The antiviral effect of this substance is postulated at a post-translational level, i.e. an inhibitory effect on the so-called budding or ejection process of the virus has been discussed. In common with α-lipoic acid, alpha interferon therefore acts on the already infected cell. To compare both compounds, freshly split Jurkat cells were infected with HIV ($8 \times 10^3$ PFU) and afterwards recombinant alpha interferon (rIF) (70 units/ml) or 35 ng/ml of α-lipoic acid was added thereto using a pipette. The experiment was concluded after 7 days in order to assess in particular the growth of the first virus generation. Both substances showed comparable inhibition of the vital replication in the infected, not pre-treated cells (FIG. 2 and 3). While rIF shows a more pronounced inhibitory effect in the reverse transcriptase test (measures the relative amount of virions produced, FIG. 2), the inhibition in the plaque test (indicates the exact number of infectious virions, FIG. 3) is clearer for α-lipoic acid. The combination of both substances shows an additive effect.

The compounds of the invention may be in particular also be combined with AZT in the treatment of AIDS since AZT possesses a different mechanism of action. AZT inhibits reverse transcriptase and thus acts predominantly on non-infected cells. However, once a cell has been infected, AZT—unlike α-lipoic acid—is no longer able to inhibit the growth of the virus.

PREPARATION OF FRESHLY INFECTED CELLS

1. As described in the case of the preparation of a cell line permanently infected with HIV-1, including point 2.
2. Cells are taken up in fresh medium and may now be defined as being freshly infected cells. As distinct from permanently infected cells, far fewer cells are virus carriers, and therefore synchronously treated, i.e. the first and second virus generation is given off into the culture supernatant relatively at the same time on the 3rd and 7th day. These virus generations may be quantified on these days (plaque and reverse transcriptase test) and may be compared. The term "single hit kinetics" is also used in this context.
3. α-lipoic acid is added using a pipette.
4. Cells are cultured for 7 days in an incubator.
5. On day 4 and day 7 samples are withdrawn from the culture for plaque and RT assay.

INHIBITION OF HIV REPLICATION BY α-LIPOIC ACID IN VIVO METHOD

Determination of the plasma p24 antigen level using a commercial ELISA; p24 is the designation for a structural protein of the HIV virus; ELISA (Enzyme Linked Immuno Sorbent Assay) is a test technique frequently used in virology in order to determine proteins, antigens, etc.

Virus isolation with cocultivation: patient lymphocytes are cocultivated with donor lymphocytes. The virus produced by these cells (p24) is measured using an ELISA after 21 days (standard method).

Virus isolation without cocultivation: the production of virus (p24) from $1 \times 10^6$ patient lymphocytes is quantitatively measured using an ELISA after 11 days. No donor lymphocytes are added in this standardized method. Virus production may be quoted in pg[1] p24/ml/200,000 cells. (Newly developed method). Cell titration: virus isolation is carried out starting from a decreasing number of patient lymphocytes (e.g. $10^6$, $10^5$, $10^4$).

Determination of the plasma titer which states the number of infectious viruses in the plasma.

[1] pg=picogram

RESULTS

The following results were recorded in 4 patients in Walter Reed stage 6. Application of α-lipoic acid was, by means of infusion of an α-lipoic acid solution having the following composition: 10 ml of aqueous solution containing 250 mg of α-lipoic acid in the form of the ethylene diamine salt (=323 mg salt) as well as 1 g of 1,2-propylene glycol and 100 mg of benzyl alcohol.

Walter Reed stages: division of HIV-infected patients according to the degree of their clinical symptoms. In stage 0 no HIV virus can be detected. Stage 6 relates to the final stage of AIDS.

Patient 1 (K.M., 64 kg; Walter Reed stage 6)

Therapy phase 58 days, $2 \times 36$ hours being interrupted because of holiday. The total dose was 258.3 g, corresponding to an average daily dose of 4.7 g/day. On 19 days doses of 3 g to less than 6 g were given; on 18 days doses of 6-8 g/day were given.

The infusion of α-lipoic acid was given through a central venous catheter over 24 hours. Because of initially non-excluded interactions with Zovirax (on account of Herpes Zoster) the α-lipoic acid infusion was interrupted during the administration of Zovirax (3 times 1-2 hours each/day).

The plasma p24 antigen level was determined and virus isolations were carried out.

The plasma p24 antigen level during the months before commencement of therapy fluctuated in a range of 0.350 ng/ml.

14 days after commencement of therapy this value fell to 0.05 ng/ml, and then fell still further until day 29 (to 0.025 ng/ml) after which it rose again to a value of 0.25 ng/ml until the end of therapy. Virus isolation (standard method) was positive throughout the entire therapy period.

Patient 2 (Ro., 50 kg, Walter Reed stage 6).

The therapy phase lasted 21 days, the pharmaceutical composition only being given on a total of 17 days. The total dose was 32 g. The dosage was 1 g on 2 days, 3 g on 8 days, 4 g on 1 day.

Plasma p24 antigen level determination, virus isolation with cell titration and plasma titration were carried out in this patient.

Prior to treatment the plasma p24 antigen level was constant at 0.4 ng/ml. Initially this value fell to barely the 10-fold value. Before treatment the cell titer was 1000, i.e. virus could be isolated from only $10^3$ cells (standard method). During the course of treatment this value fell by two orders of magnitude, i.e. the virus could only be cultivated from $10^5$ cells. Prior to therapy the plasma titer was 100. This value dropped to 0 shortly after therapy began.

Towards the end and after conclusion of therapy there was a drastic fall in all virus markers. Even virus isolation itself was repeatedly negative.

Patient 3 (Pal.; Walter Reed stage 6).

Total dose of α-lipoic acid of 104 g on 26 days during the 27-day therapy phase. The dosage administered was: on 2 days 2 g/day, on 2 days 3 g/day, on 1 day 4 g/day, on 2 days 5 g/day, on 3 days 6 g/day. After 1 day's holiday without therapy 6 g/day were given for 2 days, the dose was then reduced to 1 g for 4 days due to increasing thrombopenia. Then 1 day 3 g, 6 days 6 g/day and then, because of renewed decrease in thrombocytes (Daraprim side effect) dose reduction to 1 g for 3 days and 2 g/day for 1 day. Therapy then ended as scheduled. The maximum dose of 6 g/day was given for a total of 11 days.

In this patient the plasma p24 antigen level (always negative) was measured, virus isolation as well as plasma titrations (always negative) were carried out.

Before commencement of therapy the production of p24 antigen in pg/ml 200,000 cells was about 10. This value doubled on day 5 of the therapy to fall continuously to 0 by day 28. After the end of therapy this value rose again slowly.

Patient 4 (Pag., 75 kg; Walter Reed stage 6).

Therapy phase 19 days. Total dose of α-lipoic acid: 82.75 g. Therapy as from 22.05.1990 with α-lipoic acid permanent infusion for 20-24 hours/day. Doses: 2 days 2 g, 9 days 4 g, 1 day 3 g, 1 day 2.75 g, 3 days 6 g, 1 day 7 g, 2 days 6 g. Administration as 20-24 hour permanent infusion with 1 break of ½ day on one occasion.

All parameters (plasma p24 antigen level), virus isolation with cell titration (plasma titration) were positive in this patient and were measured in the course of therapy. The plasma p24 antigen level, which moved around values of 0.070 ng/ml shortly before and at the beginning of therapy fell up to the 18th day of therapy to 0.005 ng/ml. After the end of therapy the level again rose to the initial values.

p24 production/ml/200,000 cells shortly before therapy was 8 pg/ml. Up to the end of therapy this value fell by 75% and also did not rise significantly after the end of therapy. At this time the patient was also being treated with AZT. The plasma titer, which was 10 before commencement of therapy, fell to 0 during therapy and then settled down at 1 after the end of therapy and thereafter. Before commencement of therapy, virus was clearly detected in $2 \times 10^6$ cells. At the end of therapy hardly any viruses could be detected (in the current range). After the conclusion of therapy the results deteriorated once again.

In summary the results were as follows:

With Thioctacid therapy clearly positive plasma p24 antigen levels (case 1 and 2) fell within a short period of time (ca. 14 days) to at least 1/10 of their initial value. In the case of virus isolations from patient lymphocytes, markedly lower virus production was demonstrated in the course of therapy in three cases (case 2, 3 and 4). In two patients (case 2 and 3) the result was even totally negative. Positive plasma titers also fell to 0 in the course of therapy (case 2 and 4).

These results show that in patients displaying clearly measurable virological markers, Thioctacid therapy leads to a marked improvement in these parameters and thus that a positive effect on the entire symptomatology may be expected with longer-term treatment with α-lipoic acid.

The direction of effect of compounds of Formula I of the invention in respect of their antiretroviral action is best compared with the effect of the known pharmaceutically active substance Immuthiol (sodium diethyl dithiocarbonate). However, in contradistinction to that compound, for example, the compounds of Formula I lead to significantly more noticeable suppression of the cytopathogenic effect (CPE), particularly when the substances are added after infection of the cells.

Indications for compounds I that may for example be considered here are the therapeutic treatment of HIV-infected, asymptomatic and also symptomatically ill patients in all stages of the acquired immunodeficiency syndrome (AIDS) according to the conventional international classification. There are no counterindications.

Dosage amounts and forms of application that may be considered in addition to those already mentioned particular for use in combating retroviruses (in particular AIDS) are:

The pharmaceutical formulations for this application generally contain between 50 mg and 3 g as a single dose, preferably 100 mg to 1 g, in particular 400 mg or 500 mg to 1 g of the active component of the invention of Formula I (preferably Thioctacid or dihydrolipoic acid). The active ingredient levels/kg body weight should be between 3.5 and 200 mg, preferably between 7 and 100 mg, in particular between 35 and 70 mg/kg body weight.

Active ingredients of Formula I (that is, compound of Formula I) should be released from the formulations slowly. This also applies to the component b in combinations.

Administration may for example be in the form of tablets, capsules, pills, coated tablets, aerosols or in liquid form.

Liquid forms of application that may for example be considered are: alcoholic or aqueous solutions as well as suspensions and emulsions.

Preferred forms of application are for example tablets containing between 100 mg and 2 g or solutions containing between 10 mg to 0.2 g/ml of liquid of active substance.

The individual dose of active substances of Formula I may for example be:

(a) in the case of oral medicinal forms between 100 mg-3 g, preferably 200 mg-1 g, in particular 400 mg to 1 g.

b) in the case of parenteral medicinal forms (for example intravenous, intramuscular) between 100 mg-12 g, preferably 200 mg-6 g, in particular 500 mg to 6 g.

c) in the case of medicinal forms for inhalation (solutions or aerosols) between 100 mg-2 g, preferably 200 mg-1 g.

The doses according to a) to c) may for example be given 1 to 6 times, preferably 1 to 4 times daily or also as permanent infusion, for example using an infusoniate[2].

[2] infusion apparatus for accurate hourly dosage of the active substance in solution The daily dose of active ingredient of Formula I in humans is for example in the case of parenteral application in the range of 40-80 mg, preferably 40-60 mg per kg weight (for example intravenous permanent infusion over 24 hours). When use is over extended periods, the dose may optionally be increased, for example up to 160 mg per kg weight within 24 hours. In the case of oral application the daily dose may for example be between 40-120 mg/kg body weight (if used for longer periods also increased to 160 mg or also 200 mg per kg body weight daily); the individual dose is for example 16-20 mg per kg weight, this dose appropriately being given 4 times a day. The daily dose of active substance of Formula I is preferably 4–6 g: the pharmaceutical compositions therefore preferably contain 1–1.5 g of compound I in a galenic formulation, such a dose preferably being given 4 times.

For purposes of treatment it is, for example, possible to recommend 3 times daily 1 to 4 tablets having a content of 50 mg to 2 g, preferably 400 mg or 500 mg to 2 g of active substance or for example for intravenous injection 1 to 4 times daily one ampoule/infusion bottle of 1 to 500 ml content with 200 mg to 6 g in particular 500 mg to 6 g of active substance. In the case of oral administration the minimum daily dose is for example 300 mg; the maximum daily dose in oral administration should not exceed 12 g.

The quoted dose amounts always relate to the free acids of Formula I. Should the compounds I be used in the form of their salts the given dosages/dosage ranges should be increased in accordance with the higher molecular weight.

For the combination of active ingredients of Formula I (for example α-lipoic acid) with component b, for example AZT, the two components may in each case be mixed in a ratio of 1 to 100 to 100 to 1 equimolar parts of active substance, in particular in a ratio of 1 to 10 to 10 to 1, preferably in a ratio of 1 to 3 to 3 to 1 parts.

In the event of a combination of active substances of Formula I (for example α-lipoic acid) and α-interferon, the two components may for example be present in the following ratio: 50 mg–6 g of compound I (component a) to $8 \times 10^6$ enzyme units to $1 \times 10^5$ enzyme units α-interferon, in particular 0.5–3 g of component a to $1–4 \times 10^6$ enzyme units of α-interferon.

In the combination of active substances of Formula I and other components in accordance with b), both components may be present as a mixture. In general the components are, however, separated from one another in a galenic formulation, it being possible to use the galenic formulations known for this purpose: for example one component as tablet or lacquaered tablet, the other component as powder, both in one capsule and vice versa; one component in the form of pellets, the other as a powder, coated tablet or tablet and vice versa and where the two forms are present for example in a capsule; or in the form of multi-layered or laminated tablets. Reference is made in this context to the book by Karl Thoma, Arzneimittelstabilität, Frankfurt 1978, for example page 207 et seq.

The combination of the invention may, however, also be present as a product in which the two individual active substances are in each case present in formulations that are completely separated from one another, in particular component b, but also both components (a and b) being contained in ampoules and/or infusion bottles so that administration is possible separately or at staggered time intervals.

Should such completely separate formulations be present, these are adapted to each other and contain the corresponding active substances in the dosage unit in the same amounts and appropriate weight ratios in which they may be present in the combined mixture.

In the case of a product for separate administration, it is also possible for both combination components not to be given simultaneously. In such cases it is for example possible to give the active ingredient of Formula 1 as a permanent infusion (dose for example 2–5 g per day) and the other component b) to be given simultaneously (dose for example 50–800 mg or $1–8 \times 10^6$ enzyme units, preferably intramuscular) or also as permanent infusion per day or the active substance of Formula I may be given, for example, four times per day (individual dose for example 0.5–2 g) and the other component b) may be given simultaneously (dose for example 50–200 mg or $0.5–3 \times 10^6$ enzyme units). It is then for example possible for 1 to 3 further doses of component b) (for example between 50–200 mg or $0.5–3 \times 10^6$ enzyme units) to follow at an interval of in each case 6 and/or 12 hours.

The formulations/products of the invention may preferably also contain additional vitamins, in particular vitamin $B_1$ and/or vitamin E.

The acute toxicity of α-lipoic acid in the mouse (expressed in the LD 50 mg/kg; Method after Miller and Tainter: Proc. Soc. Exper. Biol. a. Med. 57 (1944) 261) is, for example, in oral application above 400 mg/kg body weight, that of dihydrolipoic acid above 200 mg/kg body weight mouse.

DETAILED DESCRIPTION OF PREFERRED EMBODIMENTS

The invention is illustrated by the following examples.

Example 1

Tablets containing 50 mg S- or R- α-lipoic acid 250 g S- α-lipoic acid are evenly ground with 750 g microcrystalline cellulose. After sieving the mixture, 250 g starch (starch 1500/ Colorcon), 732.5 g lactose, 15 g magnesium stearate and 2.5 g highly disperse silicon dioxide are mixed therein and the mixture is pressed into tablets weighing 400.0 mg.

Each tablet contains 50 mg S- α-lipoic acid.

In the same way it is possible to prepare tablets with 50 mg R- α-lipoic acid by using the same amount of R-α-lipoic acid instead of 250 g of S- α-lipoic acid.

The tablets may optionally be provided with a gastric juice-soluble or gastric juice-permeable film coating using conventional processes.

Example 2

Ampoules containing 50 mg S- or R- α-lipoic acid as tromethamine salt in 2 ml 250 g S- α-lipoic acid are dissolved together with 352.3 g tromethamine (2-amino-2-(hydroxymethyl)-1,3-dihydroxypropane) in a mixture of 9 liters of water for injection purposes and 200 g 1,2-propylene glycol with stirring. The solution is made up to 10 liters with water for injection purposes and then filtered through a membrane filter of pore size 0.2 μm with glass fiber prefilter. The filtrate is filled under aseptic conditions in 2 ml batches into sterilized 2 ml ampoules.

Each ampoule contains 50 mg S- α-lipoic acid as tromethamine salt in 2 ml injection solution.

In the same way it is possible to prepare ampoules with R- α-lipoic acid by using the same amount of R-α-lipoic acid instead of 250 g S- α-lipoic acid.

Example 3

Ampoules containing 250 mg dihydrolipoic acid in 10 ml injection solution 60 g tromethamine and 1 g ethylene diamine tetraacetic acid, disodium salt are dissolved in 1.8 liters of water for injection purposes. Nitrogen is passed through the solution 30 minutes. With continued flow of nitrogen, 2 g sodium disulphite and then 50 g dihydrolipoic acid are dissolved in the mixture. The solution is diluted up to a volume of 2 liters using water for injection purposes through which nitrogen has been passed. After careful mixing, the solution is filtered through a membrane filter of pore size 0.2 μm and the filtrate is filled under aseptic conditions and with pre- and post-gassing with nitrogen into ampoules of 10 ml filling volume each.

Each ampoule contains 250 mg dihydrolipoic acid as tromethamine salt in 10 ml solution.

What is claimed is:

1. A dosage unit of a pharmaceutical composition containing at least one compound of Formula I, where X is a hydrogen atom and both X's represent a direct link between the two sulphur atoms; Y is hydrogen or a $C_1$–$C_6$-alkyl and n represents a number from 1 to 10 with the exception to α-lipoic acid and dihydrolipoic acid, or a pharmaceutically acceptable salt of said compound of Formula I
the dosage unit being a solid or semi-solid formulation containing 20 mg to 6 g of the total amount of active ingredient of Formula I, or the dosage nit being a solution, suspension or emulsion which contains 0.2 mg to 800 mg per ml, of the total amount of active ingredient of Formula I.

2. A solid or semi-solid dosage unit as set forth in claim 1 which contains 50 mg to 2 g of the total amount of active ingredient of Formula I.

3. A solid or semi-solid dosage unit as set forth in claim 1 which contains 100 mg to 1 g of the total amount of active ingredient of Formula I.

4. A solution, suspension or emulsion as set forth in claim 1 which contains 10 mg to 500 mg per ml, of the total amount of active ingredient of Formula I.

5. A solution, suspension or emulsion as set forth in claim 1 which contains 40 mg to 200 mg per ml, of the total amount of active ingredient of Formula I.

6. A dosage unit of a pharmaceutical composition containing α-lipoic acid, the dosage unit being a solid or semi-solid formulation containing 51 mg to 6 g α-lipoic acid or a pharmaceutically acceptable salt thereof or an injection solution which contains 26 mg to 500 mg per ml α-lipoic acid or a pharmaceutically acceptable salt thereof, or a drinkable solution, suspension or emulsion which contains 1 mg to 500 mg per ml of α-lipoic acid or a pharmaceutically acceptable salt thereof.

7. A dosage unit of a solid or semi-solid pharmaceutical composition as set forth in claim 6 containing 100 mg to 2 g α-lipoic acid or a pharmaceutically acceptable salt thereof.

8. A dosage unit of a solid or semi-solid pharmaceutical composition as set forth in claim 6 containing 200 mg to 1 g α-lipoic acid or a pharmaceutically acceptable salt thereof.

9. An injection solution as set forth in claim 6 which contains 50 mg to 200 mg per ml α-lipoic acid or a pharmaceutically acceptable salt thereof, 10. An injection solution as set forth in claim 6 which contains 100 mg per ml of α-lipoic acid or a pharmaceutically acceptable salt thereof.

11. A drinkable solution, suspension or emulsion as set forth in claim 6 which contains 1 mg to 50 mg per ml of α-lipoic acid or a pharmaceutically acceptable carrier thereof.

12. A drinkable solution, suspension or emulsion as set forth in claim 6 which contains 5 mg to 10 mg per ml of α-lipoic acid or a pharmaceutically acceptable salt thereof and a liquid, pharmaceutically acceptable carrier therefor.

13. A dosage unit of a pharmaceutical composition containing dihydrolipoic acid in which the dosage unit is a solid or semi-solid formulations which contains 601 mg to 6 g dihydrolipoic acid or a pharmaceutically acceptable salt thereof, or a solution, suspension or emulsion which contains 182 mg/ml to 1137 mg/ml dihydrolipoic acid or a pharmaceutically acceptable salt thereof.

14. A solid or semi-solid dosage unit as set forth in claim 13 which contains 610 mg to 2 g dihydrolipoic acid or a pharmaceutically acceptable salt thereof.

15. A solid or semi-solid dosage unit as set forth in claim 13 which contains 650 mg to 1 g dihydrolipoic acid or a pharmaceutically acceptable salt thereof.

16. A solution, suspension or emulsion as set forth in claim 13 which contains 200 mg/ml to 1000 mg/ml dihydrolipoic acid or a pharmaceutically acceptable salt thereof.

17. A solution, suspension or emulsion as set forth in claim 13 which contains 300 mg/ml to 500 mg/ml dihydrolipoic acid or a pharmaceutically acceptable salt thereof.

18. A pharmaceutical composition as set forth in claim 1 which contains a conventional pharmaceutical carrier substance, auxiliary substance, stabilizer, solubilizer and/or diluent.

19. A pharmaceutical composition according to claim 1 which contains additional vitamins.

20. A method of treating a disorder caused by a retrovirus which comprises administering an effective amount of a pharmaceutical composition which contains a compound of Formula I, 21. A method as set forth in claim 20 in which the compound of Formula I is administered in an amount sufficient to produces an active daily level in the body between 3.5 and 200 mg/kg body weight.

22. A dosage unit as set forth in claim 1 in which X is a hydrogen atom.

* * * * *